United States Patent
Ochoa Gomez et al.

(10) Patent No.: US 9,540,390 B2
(45) Date of Patent: Jan. 10, 2017

(54) METHOD FOR MANUFACTURING 1,4:3,6-DIANHYDROHEXITOL DI(ALKYL CARBONATE)S

(71) Applicant: FUNDACION TECNALIA RESEARCH & INNOVATION, Donostia-San Sebastian (ES)

(72) Inventors: Jose Ramon Ochoa Gomez, Donostia-San Sabastian (ES); Silvia Gil Rio, Donostia-San Sabastian (ES); Belen Maestro Madurga, Donostia-San Sebastian (ES); Leire Lorenzo Ibarreta, Donostia-San Sebastian (ES); Olga Gomez De Miranda Jimenez De Aberasturi, Donostia-San Sebastian (ES)

(73) Assignee: Fundacion Technalia Research & Innovation, Donostia-San Sebastian (ES)

( * ) Notice: Subject to any disclaimer, the term of this patent is extended or adjusted under 35 U.S.C. 154(b) by 0 days.

(21) Appl. No.: 14/760,490

(22) PCT Filed: Jan. 24, 2013

(86) PCT No.: PCT/ES2013/070030
§ 371 (c)(1),
(2) Date: Jul. 13, 2015

(87) PCT Pub. No.: WO2014/114823
PCT Pub. Date: Jul. 31, 2014

(65) Prior Publication Data
US 2015/0336978 A1    Nov. 26, 2015

(51) Int. Cl.
*C07D 493/04*   (2006.01)
(52) U.S. Cl.
CPC .................. *C07D 493/04* (2013.01)
(58) Field of Classification Search
CPC .................................................. C07D 493/04
See application file for complete search history.

(56) References Cited

U.S. PATENT DOCUMENTS

| 8,399,601 B2 * | 3/2013 | Fuertes ............... C07D 493/04 528/352 |
| 2004/0241553 A1 | 12/2004 | Abe et al. |
| 2012/0041169 A1 | 2/2012 | Fuertes et al. |

FOREIGN PATENT DOCUMENTS

JP    H06261774 A    9/1994

OTHER PUBLICATIONS

Fuertes et al (2011): STN International, HCAPLUS database (Columbus, Ohio), Accession No. 2011: 437003.*
International Search Report received in PCT Application No. PCT/ES2012/070030 mailed May 6, 2013.
Tundo et al., "Green Synthesis of Dimethyl Isosrbide", Chemsuschem, vol. 3, No. 5, pp. 566-570, ISSN: 1864-5631, DOI: 10.1002, (May 2010).

* cited by examiner

*Primary Examiner* — Golam M M Shameem
(74) *Attorney, Agent, or Firm* — Miles & Stockbridge P.C.; Ajay A. Jagtiani

(57) ABSTRACT

The present invention relates to a process for the manufacturing of pure and substantially oligomers-free 1,4:3,6-dianhydrohexitol di(alkyl carbonate)s which comprises the steps of: a) Preparing a reaction mixture consisting of at least one dianhydrohexitol, at least 2 molar equivalents with respect to the amount of dianhydrohexitol present, of at least one dialkyl carbonate of formula R—O—C(=O)—O—R, where R has the same meaning indicated above, and from 0.01 to less than 0.1 molar equivalents of a transesterification catalyst with respect to the amount of dianhydrohexitol present; and b) Heating the reaction mixture up to its reflux temperature in a reactor preferably equipped with a rectification column comprising a number of theoretical distillation plates sufficient to separate continuously from the reaction mixture by fractional distillation the alcohol obtained or the azeotrope which the alcohol forms with the dialkyl carbonate present in the reaction mixture. The process comprises further recovering the transesterification catalyst from the reaction mixture and isolating the 1,4:3,6-dianhydrohexitol di(alkyl carbonate).

18 Claims, No Drawings

METHOD FOR MANUFACTURING 1,4:3,6-DIANHYDROHEXITOL DI(ALKYL CARBONATE)S

FIELD OF THE INVENTION

The present invention is related to an improved process for manufacturing pure 1,4:3,6-dianhydrohexitol di(alkyl carbonate)s substantially free of oligomers by transesterification of a dialkyl carbonate with a 1,4:3,6-dianhydrohexitol. The 1,4:3,6-dianhydrohexitol di(alkyl carbonate)s of the present invention are useful for preparing synthetic polymers such as polycarbonates and non-isocyanate polyurethanes.

BACKGROUND OF THE INVENTION

Processes for synthesizing dianhydrohexitol di(alkyl carbonate)s have been described in the patent application US 2004/241553 and in the Japanese document JP 6-261774 by reaction between a dianhydrohexitol and a chloroformate ester. However, a major disadvantage of such processes is the use of toxic compounds such as the chloroformate esters.

A safer and environmental benign transesterification process avoiding toxic reactants is described in the patent application US 2012/0041169 in which a 1,4:3,6-dianhydrohexitol, particularly isosorbide, is reacted with a dialkyl carbonate, preferably dimethyl carbonate (DMC) and diethyl carbonate (DEC), in the presence of a transesterification catalyst, such as a base, preferably potassium carbonate ($K_2CO_3$) lithium hydroxide (LiOH) and potassium hydroxide (KOH) and to give the corresponding 1,4:3,6-dianhydrohexitol di(alkyl carbonate) in good yields shifting the equilibrium to right by distilling continuously the alcohol or the azeotrope formed. However, a drawback of this process is that a high fraction of oligomers (oligocarbonates) is formed as by-products, at the expense of the desired 1,4:3,6-dianhydrohexitol di(alkyl carbonate), in particular when a relatively low dialkyl carbonate/dianhydrohexitol molar ratio is used, for example of less than or equal to 20 or 10. According to US 2012/0041169, in order to limit the oligomer fraction to approximately 5% of the solvent-free reaction mixture, a molar excess of dialkyl carbonate greater than 40 must be used which leads to a lower productivity and, hence, to an undesirable increase in the production plant size. Furthermore, the greater the excess of dialkyl carbonate used the more energy will be consumed to remove this chemical from the reaction mixture by evaporation at the end of the transesterification reaction. Moreover, to obtain a 99% pure 1,4:3,6-dianhydrohexitol di(alkyl carbonate) a costly purification step either by distillation under high vacuum (<1 mbar) or by crystallization is employed. Likewise, another drawback of this process is the high amount of catalyst used, comprised between 0.1 and 10 molar equivalents which is very particularly between 1 and 3 molar equivalents with respect to the amount of dianhydrohexitol.

In view of the above, there is still the need in the state of the art of providing an improved process for manufacturing 1,4:3,6-dianhydrohexitol di(alkyl carbonate)s which overcomes at least part of these drawbacks.

DETAILED DESCRIPTION OF THE INVENTION

As above stated, a main drawback of the procedure disclosed in the patent application US 2012/0041169 is that up to 5% of oligomers are obtained as by-products together with the desired 1,4:3,6-dianhydrohexitol di(alkyl carbonate). However, the percentage of oligomers is calculated in US 2012/0041169 as based on area distributions by gas chromatography with the solvent being excluded. As it is show in Examples 1 to 6 further below, this analytical procedure seriously underrates the percentage of oligomers because the oligomers of higher polymerization degree are not detected due to their high boiling points. The method used by the present inventors, gel permeation chromatography (GPC), is a more suitable and accurate method for the oligomers determination as confirmed by the instant patent application. As shown in the Examples 1 to 4, GPC results indicate that using the amounts of catalyst disclosed in patent application US 2012/0041169, the amounts of oligomers obtained are above 17%.

Surprisingly, the present inventors have discovered that such an amount of oligomers can be substantially reduced by using an amount of a transesterification catalyst comprised between 0.01 and less than 0.1, preferably between 0.01 and 0.09, more preferably between 0.01 and 0.07, even more preferably between 0.01 and 0.05, and most preferably between 0.01 to 0.03 molar equivalents of catalyst with respect to the amount of dianhydrohexitol present. Moreover, 1,4:3,6-dianhydrohexitol di(alkyl carbonate) is obtained with higher yields.

Additional advantages of using such low quantities of a catalyst are less raw material consumption, less energy consumption due to stirring of the reaction mixture and an easier separation of the catalyst by filtration, when solid heterogeneous catalysts are used. Without wishing to be bound by any theory, the present inventors hypothesize that at these low catalyst concentrations the rate of 1,4:3,6-dianhydrohexitol di(alkyl carbonate) conversion into oligomers (oligocarbonates) by polycondensation is dramatically reduced relative to the rate of 1,4:3,6-dianhydrohexitol di(alkyl carbonate) formation resulting in a much lower amount of oligomers as by-products relative the procedure of the prior art.

Thus, the present invention is related to a process for the manufacturing of pure and substantially oligomers-free 1,4:3,6-dianhydrohexitol di(alkyl carbonate)s of formula (I):

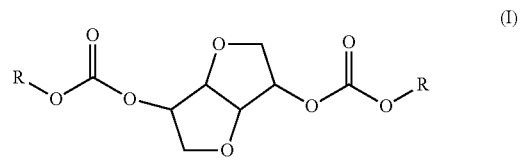

where each R independently represents a linear or branched alkyl group, preferably a $C_1$-$C_6$ alkyl group, in particular a methyl or ethyl group, said process comprising the steps of:

(a) Preparing a reaction mixture consisting of at least one dianhydrohexitol, at least 2 molar equivalents with respect to the amount of dianhydrohexitol present, of at least one dialkyl carbonate of formula R—O—C(=O)—O—R, where R has the same meaning indicated above, and from 0.01 to less than 0.1 molar equivalents of a transesterification catalyst with respect to the amount of dianhydrohexitol present; and (b) Heating the reaction mixture up to its reflux temperature in a reactor preferably equipped with a rectification column comprising a number of theoretical distillation plates sufficient to separate continuously from the reaction mixture by fractional distillation the alcohol obtained or the azeotrope which the alcohol forms with the dialkyl carbonate present in the reaction mixture.

The process of the invention further comprises recovering substantially all the transesterification catalyst from the reaction mixture, which can be recycled in the following reaction. Subsequently, the process of the invention comprises further isolating the 1,4:3,6-dianhydrohexitol di(alkyl carbonate), which comprises removing the unreacted dialkyl carbonate from the reaction mixture by evaporation at ambient pressure or under vacuum.

The term "1,4:3,6-dianhydrohexitol" or "dianhydrohexitol" used in the present invention encompasses isosorbide, isomannide and isoidide, with isosorbide being the selected dianhydrohexitol according to a particular embodiment.

By "substantially oligomers-free" or "substantially free of oligomers" it is meant that the concentration of oligomers in the isolated (after removal of the catalyst and the unreacted dialkyl carbonate) 1,4:3,6-dianhydrohexitol di(alkyl carbonate) is lower than 14%, preferably 10%, more preferably lower than 5%, and even more preferably lower than 1%.

By "in quantitative yields" it is meant that the yield of isolated 1,4:3,6-dianhydrohexitol di(alkyl carbonate) is higher than 86%, preferably higher than 90%, more preferably higher than 95%, and even more preferably higher than 99%.

By "pure 1,4:3,6-dianhydrohexitol di(alkyl carbonate)" it is meant that the purity of the isolated 1,4:3,6-dianhydrohexitol di(alkyl carbonate) is higher than 85%, preferably higher than 90%, more preferably higher than 95%, and even more preferably higher than 99%.

By "recovering substantially all the transesterification catalyst from the reaction mixture" it is meant that at least 95% of the initial amount of catalyst is recovered at the end of the reaction, preferably at least 98% and more preferably at least 99%.

The dialkyl carbonate/dianhydrohexitol molar ratio in the starting reaction mixture prepared in step (a) is at least 2, particularly between 5 and 50, more particularly between 5 and 40, and even more particularly between 10 and 35. Oligomers formation is generally favored by lower molar ratios, while higher values result in higher energy consumption during the step of isolating the 1,4:3,6-dianhydrohexitol di(alkyl carbonate).

The transesterification catalyst used in the process of the present invention is according to a particular embodiment a basic catalyst chosen from one or more of the following: alkali metal and alkaline earth metal carbonates and hydrogencarbonates, alkali metal and alkaline earth metal hydroxides, alkali metal and alkaline earth metal phosphates, hydrogenphosphates and dihydrogenphosphates, ammonium salts chosen from ammonium carbonates, hydrogencarbonates, hydroxides, phosphates, hydrogenphosphates and dihydrogenphosphates and amines in particular tertiary alkylamines. The preferred basic catalysts are solids and more preferred are those leading to a heterogeneous-phase catalytic process in order to facilitate their recovery from the reaction mixture by filtration at the end of the reaction, and consequently to facilitate their recycling to the process as well. Much more preferably, the transesterification catalyst is one or more of potassium carbonate, cesium carbonate, potassium hydroxide and lithium hydroxide, with potassium carbonate and cesium carbonate being the most preferred.

The starting reaction mixture prepared in step (a) comprises from 0.01 to less than 0.1 molar equivalents, preferably between 0.01 and 0.09, more preferably between 0.01 and 0.07, even more preferably between 0.01 and 0.05, and most preferably between 0.01 and 0.03 molar equivalents of catalyst with respect to the amount of dianhydrohexitol present. Values lower than 0.01 slow down dramatically the reaction rate, while above 0.1 molar equivalents the amount of oligomers formed is significant.

The reaction used in the process of the present invention is a transesterification which is illustrated in Scheme 1 for isosorbide and dimethyl carbonate.

Scheme 1

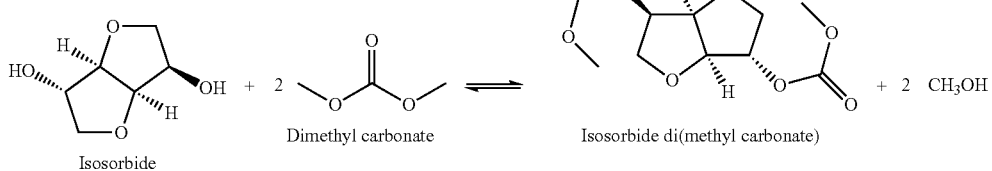

Isosorbide    Dimethyl carbonate    Isosorbide di(methyl carbonate)    + 2 CH₃OH Consequently, it is an equilibrium reaction and, therefore, in order to achieve dianhydrohexitol conversions of about 100% and 1,4:3,6-dianhydrohexitol di(alkyl carbonate) in high yields the equilibrium must be shifted to the right by distilling continuously the alcohol formed in the transesterification reaction or the azeotrope which the alcohol may form with the dialkyl carbonate. The continuous distillation can be carried out either under reduced pressure or under atmospheric pressure, preferably under atmospheric pressure. The distillation can be carried out using a rectifying column with enough theoretical plates to remove at the top of the column a stream enriched in the alcohol formed in the transesterification reaction, or a stream enriched in the azeotrope formed by the alcohol and the dialkyl carbonate, as it is the case for example when dimethyl carbonate is used.

As distillation proceeds, the temperature of the reaction mixture increases continuously from a value corresponding to the boiling point of the reaction mixture or the azeotrope formed to a value corresponding to the boiling point of the dialkyl carbonate used at the reaction pressure. This point indicates that reaction is over, i.e. step (b) of the process of the present invention is over. Alternatively, the final time of the reaction can be detected by Fourier transform infrared spectroscopy (FTIR) by monitoring the disappearance of a characteristic band. In the Example of Scheme 1, the isosorbide hydroxyl band at 3392 cm$^{-1}$ versus time can be monitored, and when there is no hydroxyl band the reaction is over.

As above stated the process of the invention comprises further the removal of the transesterification catalyst from the reaction mixture to avoid the formation of oligomers during the next process step of the invention.

Subsequently, the process of the invention comprises further isolating the 1,4:3,6-dianhydrohexitol di(alkyl carbonate), which comprises removing the unreacted dialkyl carbonate from the reaction mixture by evaporation at ambient pressure or under vacuum.

In a preferred embodiment, the basic catalyst is solid and insoluble in the reaction mixture and, hence, it can be easily removed from the reaction medium by filtration. Then, the resulting filtrate is further submitted to evaporation at ambient pressure or under vacuum yielding the desired 1,4:3,6-dianhydrohexitol di(alkyl carbonate).

The so obtained 1,4:3,6-dianhydrohexitol di(alkyl carbonate) can be further submitted to one or more conventional purification steps if desired, such as one or more recrystallization steps from a suitable solvent or to distillation.

The process of the present invention is illustrated below by reference to the examples which are intended to be only illustrative and are not construed to limit the present invention in any way.

EXAMPLES

General Procedure of Synthesis of Isosorbide Di(Methyl Carbonate)

10 g of isosorbide (0.0674 mol), and the amounts of dimethyl carbonate (DMC) and catalyst (potassium or cesium carbonate) required to give the concentrations specified in the examples are introduced into a 100 mL glass reactor fitted with a magnetic stirrer, a thermometer and a reflux condenser. The reaction mixture is heated at the reflux temperature under stirring for 0.5 h in a glycerol bath kept at 100° C. Over this period of time, temperature of the reaction mixture decreases continuously indicating that methanol is being formed. Then, the reflux condenser is replaced by an 18 theoretical plates Vigreux rectifying column connected to a condenser and the reaction proceeds by continuously distilling the methanol, or the methanol/DMC mixture, until the temperature of the reaction mixture reaches the one corresponding to the boiling point of DMC (90° C.). The heat flow to the reaction mixture is adjusted so that the temperature of the vapors at the top of column is always below 75° C. in order to avoid an excessive loss of DMC. Reaction is completed when no hydroxyl band is observed by FTIR. Then, the reaction mixture is cooled at room temperature and the catalyst is removed by filtration, the cake is washed with DMC and the combined filtrates are evaporated under vacuum to yield a residue that was identified by $^1$H-NMR, $^{13}$C-NMR, and elemental analysis as isosorbide di(methyl carbonate). The percentage of oligomers was determined by GPC and was dependent of the catalyst concentration. The catalyst is recovered in 99% yield, at least.

NMR spectra were recorded in a 400 MHz BRUKER AC NMR spectrometer using tetramethylsilane as internal reference and deuterated dimethyl sulfoxide as solvent. FTIR spectra were recorded using a Perkin Elmer Spectrum 2000 spectrometer. Elemental analyses were carried out in a Thermo Finnigan 1112 Series Flash Elemental Analyzer (ThermoFisher Scientific).

The following data are referred to the isosorbide di(methyl carbonate) of the example 6 below:

Elemental analysis: Found (%): C, 45.94; H, 5.36. Calc. (%) for $C_{10}H_{14}O_8$: C, 45.81; H, 5.38.

FTIR $v_{max}$/cm$^{-1}$ (film): 2961, 2880, 1749, 1444, 1349, 1263, 1100, 1053, 1011, 973, 933, 887, 867, 791.

$^1$H NMR (400 MHz, DMSO-6$_d$; Me$_4$Si) δ (ppm) 5.03 (c, 1H, CH), 4.97 (dd, 1H, CH), 4.81 (t, 1H, CH), 4.46 (d, 1H, CH), 3.94 (dd, 1H (CH—O)), 3.80-3.81 (d, 3H, CH$_2$+1 H from CH$_2$), 3.72 (s, 3H, OCH$_3$), 3.71 (s, 3H, OCH$_3$).

$^{13}$C NMR (100 MHz, DMSO-6$_d$; Me$_4$Si) δ (ppm) 55.61 (OCH$_3$); 55.69 (OCH$_3$); 71.12 (CH$_2$—O); 73.09 (CH$_2$—O); 77.54 (CH—O); 81.44 (CH—O); 81.56 (CH—O); 86.09 (CH—O); 155.15 (C=O); 155.39 (C=O).

The amount of residual isosorbide was analyzed by HPLC using an UV detector, and the content of oligomers by GPC (gel permeation chromatography) using a Polymer Laboratories equipment model PL-GPC-50 Plus fitted with a refractive index detector. Eluent was tetrahydrofuran and polystyrene standards from Easy Cal PS-2 were used to obtain a molecular weight versus elution time calibration curve with a 300×7.5 mm Resipore column at 40° C. Content of oligomers was also determined by Gas Chromatography (GC) using a Varian equipment model 450-GC fitted with a FID detector and a 30 m×0.250 m×0.25 μm DB-WAX column. Injector and detector temperatures were 225° C. and 250° C., respectively. Oven temperature started at 80° C. (2 min) and was increased at 15° C./min up to 260° C. and then kept at this temperature for 5 min. Helium at 1 mL/min was used as the carrier gas and ethylene glycol as an internal standard. The split ratio was 1:10 and sample concentration was 2 g/L in acetonitrile with an injection volume of 10 μL. Time analysis was 19 min. Isosorbide di(methyl carbonate) and oligomers contents were calculated as percentages corresponding to area distributions as done in Patent Application US 2012/0041169.

Examples 1-6

Synthesis of Isosorbide Di(Methyl Carbonate) (IDMC)

Examples 1 to 6 were carried following the general synthetic procedure above stated using 61.3 g of dimethyl carbonate (10 molar equivalents relative to isosorbide) and different concentrations of potassium carbonate as given in Table 1, wherein results are also reported. As it can be seen in Table 1 by comparing the oligomer percentages obtained by GPC and GC, this last analytical technique is not suitable for analyzing oligomer contents in the product because it underrates their levels.

Using now GPC results, catalyst concentrations as the ones claimed in Patent Application US 2012/0041169 were used in examples 1-4 leading to oligomers percentages of 17.5% and higher, and not below 5% as reported is such an application.

GPC results in Table 1 show that the mean polymerization degree (Nm) of the obtained product decreases as catalyst concentration decreases and, consequently, the monomer (isosorbide di(methyl carbonate)) percentage increases when catalyst concentration decreases.

Results clearly demonstrate that catalyst concentrations lower than 10 mol % (examples 5 and 6) render isosorbide di(methyl carbonate) with a content of oligomers below 14%.

TABLE 1

DMC/isosorbide molar ratio = 10.

| Example | [K₂CO₃] (mol % vs. isosorbide) | C (%) | Nm | GPC IDMC | GPC Oligomers | GC IDMC | GC Oligomers |
|---|---|---|---|---|---|---|---|
| 1 | 150 | 100 | 1.21 | 79.4 | 20.6 | 96.2 | 3.8 |
| 2 | 100 | 100 | 1.19 | 81.2 | 18.8 | 93.4 | 6.6 |
| 3 | 50 | 100 | 1.18 | 82.0 | 18.0 | 96.8 | 3.2 |
| 4 | 10 | 100 | 1.17 | 82.5 | 17.5 | 95.7 | 4.3 |
| 5 | 2 | 100 | 1.14 | 86.4 | 13.6 | 95.9 | 4.1 |
| 6 | 1 | 100 | 1.11 | 89.3 | 10.7 | 96.5 | 3.5 |

[K₂CO₃]: potassium carbonate concentration (mol % vs. isosorbide); C: isosorbide conversion; Nm: mean polymerization degree of product; IDMC: isosorbide di(methyl carbonate); GC: Gas Chromatography.

Examples 7-9

The general procedure used in examples 1-6 was used, except that the DMC/isosorbide molar ratio (MR) was 20, 30 and 40, and the K₂CO₃ concentration was 2 mol % vs. isosorbide. Results are given in Table 2. As it can be seen, oligomer content decreases when MR increases but the positive influence of the increase in MR is much lower than that of decreasing catalyst concentration.

TABLE 2

K₂CO₃ concentration = 2 mol % vs. isosorbide. IDMC and oligomers concentrations are given in percentages as obtained by GPC.

| Example | DMC/isosorbida molar ratio | C (%) | Nm | IDMC | Oligomers |
|---|---|---|---|---|---|
| 5 | 10 | 100 | 1.14 | 86.4 | 13.6 |
| 7 | 20 | 100 | 1.09 | 91.0 | 9.0 |
| 8 | 30 | 100 | 1.08 | 92.1 | 7.9 |
| 9 | 40 | 100 | 1.07 | 92.7 | 7.3 |

C: isosorbide conversion;
Nm: mean polymerization degree of product;
IDMC: isosorbide di(methyl carbonate).

Examples 10-11

The general procedure above described was employed but using cesium carbonate as catalyst instead potassium carbonate and the DMC/isosorbide molar ratios and cesium carbonate concentrations specified in Table 3, wherein results are also reported.

As it can be seen in Table 3, when cesium carbonate concentration is 100 mol % vs. isosorbide the amount of isosorbide di(methyl carbonate) obtained (example 11, 82.2%) is somewhat lower than that obtained with potassium carbonate under the same conditions (example 5, 86.4%) but, in any case, the amount of oligomers is again high: 17.8%.

On the contrary, by lowering the amount of cesium carbonate to 2 mol % vs. isosorbide and increasing the DMC/isosorbide molar ratio to 30, the amount of oligomers decreases dramatically to less than 5%.

TABLE 3

Results obtained with cesium carbonate as catalyst.

| Example | [Cs₂CO₃] (mol % vs. isosorbide) | DMC/ isosorbide molar ratio | C (%) | Nm | IDMC | Oligomers |
|---|---|---|---|---|---|---|
| 10 | 2 | 30 | 100 | 1.04 | 95.7 | 4.3 |
| 11 | 100 | 10 | 100 | 1.18 | 82.2 | 17.8 |

C: isosorbide conversion; Nm: mean polymerization degree of product; IDMC: isosorbide di(methyl carbonate).

The invention claimed is:

1. A process for the manufacturing of pure and substantially oligomers-free 1,4:3,6-dianhydrohexitol di(alkyl carbonate)s of formula (I):

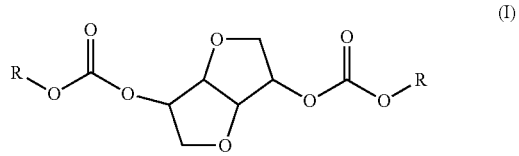

(I)

where each R independently represents one selected from a linear or branched alkyl group, a $C_1$-$C_6$ alkyl group, and a methyl or ethyl group, said process comprising the steps of:
preparing a reaction mixture consisting of at least one dianhydrohexitol, at least 2 molar equivalents with respect to the amount of dianhydrohexitol present, of at least one dialkyl carbonate of formula R—O—C(═O)—O—R, where R has the same meaning indicated above, and from 0.01 to less than 0.1 molar equivalents of a transesterification catalyst with respect to the amount of dianhydrohexitol present; and
heating the reaction mixture up to its reflux temperature in a reactor equipped with a rectification column including a number of theoretical distillation plates sufficient to separate continuously from the reaction mixture by fractional distillation the alcohol obtained or the azeotrope which the alcohol forms with the dialkyl carbonate present in the reaction mixture.

2. The process according to claim 1, wherein the final time of the reaction in the heating step is detected by monitoring by Fourier transform infrared spectroscopy the disappearance of a hydroxyl band of the at least one dianhydrohexitol.

3. The process according to claim 1, further comprising the step of:
recovering substantially all the transesterification catalyst from the reaction mixture.

4. The process according to claim 1, further comprising:
isolating the 1,4:3,6-dianhydrohexitol di(alkyl carbonate)s.

5. The process according to claim 1, wherein the reaction mixture prepared in the preparing step comprises 0.01 to 0.09 of the transesterification catalyst with respect to the amount of dianhydrohexitol present in the reaction mixture.

6. The process according to claim 1, wherein the reaction mixture prepared in the preparing step comprises from between 5 to 50 molar equivalents of dialkyl carbonate with respect to the initial amount of dianhydrohexitol.

7. The process according to claim 1, wherein the dianhydrohexitol is selected form the group consisting of isosorbide, isomannide and isoidide.

8. The process according to claim 7, wherein the dianhydrohexitol is isosorbide.

9. The process according to claim 1, wherein the transesterification catalyst is a basic catalyst.

10. The process according to claim 9, wherein the basic catalyst is solid and insoluble in the reaction mixture.

11. The process according to claim 10, wherein the transesterification catalyst is selected from the group consisting of potassium carbonate, cesium carbonate, potassium hydroxide and lithium hydroxide.

12. The process according to claim 11, wherein the transesterification catalyst is potassium carbonate.

13. The process according to claim 11, wherein the transesterification catalyst is cesium carbonate.

14. The process according to claim 1, wherein the reaction mixture prepared in the preparing step comprises from between 5 and 40 molar equivalents of dialkyl carbonate with respect to the initial amount of dianhydrohexitol.

15. The process according to claim 1, wherein the reaction mixture prepared in the preparing step comprises between 10 and 35 molar equivalents of dialkyl carbonate with respect to the initial amount of dianhydrohexitol.

16. The process according to claim 5, wherein the reaction mixture prepared in the preparing step comprises 0.01 to 0.07 molar equivalents of the transesterification catalyst with respect to the amount of dianhydrohexitol present in the reaction mixture.

17. The process according to claim 5, wherein the reaction mixture prepared in the preparing step comprises 0.01 to 0.05 molar equivalents of the transesterification catalyst with respect to the amount of dianhydrohexitol present in the reaction mixture.

18. The process according to claim 5, wherein the reaction mixture prepared in the preparing step comprises 0.01 to 0.03 molar equivalents of the transesterification catalyst with respect to the amount of dianhydrohexitol present in the reaction mixture.

* * * * *